United States Patent [19]

Teass, Jr.

[11] 4,196,383

[45] Apr. 1, 1980

[54] COAXIAL DIFFERENTIAL PH SYSTEM

[76] Inventor: Horace A. Teass, Jr., 25 Mead Rd., Armonk, N.Y. 10504

[21] Appl. No.: 903,788

[22] Filed: May 8, 1978

[51] Int. Cl.² .......................................... G01N 27/42
[52] U.S. Cl. ................................................. 324/438
[58] Field of Search ............ 204/1 T, 195 R; 324/29, 324/30 R

[56] References Cited
U.S. PATENT DOCUMENTS

Re. 27668  6/1973  Soltz et al. ..................... 324/30 R
3,441,490  4/1969  Johansson ........................ 324/30 R Primary Examiner—M. Tokar
Attorney, Agent, or Firm—Peck & Peck

[57] ABSTRACT

A circuit for measuring the PH of fluids includes a coaxial symmetrical probe having a PH probe surrounded by a reference probe; the conductor on which the PH signal passes from the probe to the control panel is within a shield to which is applied the PH voltage; and the differential amplifiers which receive and process the PH and reference signals are mounted on a conductive surface to which is applied the PH voltage.

5 Claims, 1 Drawing Figure

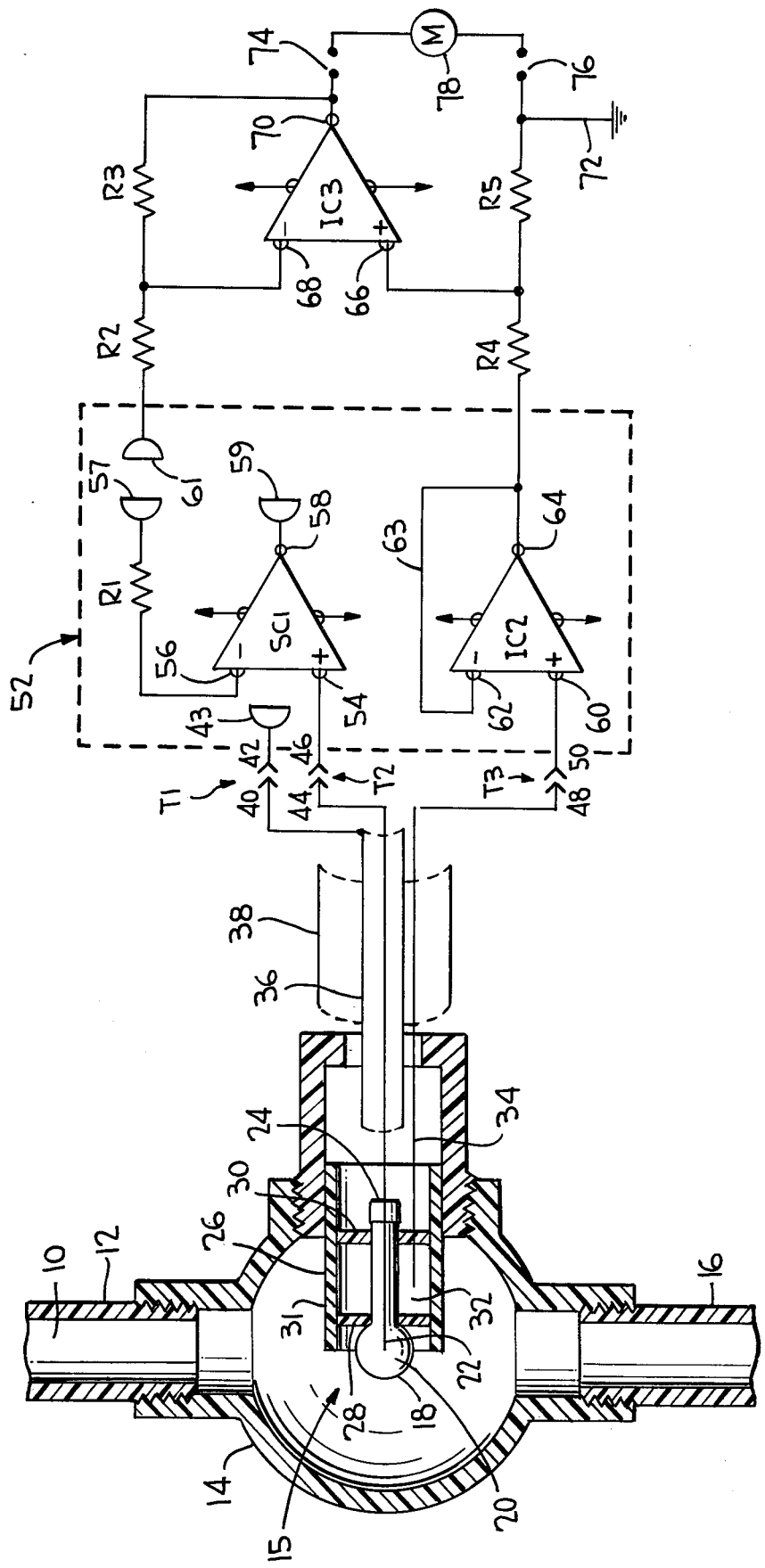

COAXIAL DIFFERENTIAL PH SYSTEM

BACKGROUND OF THE INVENTION

The present invention relates generally to measuring systems and, more particularly, to a circuit useful for measuring the PH of fluids.

Systems for the laboratory and industrial measurement of PH have been in use for many years. However, it was early realized that the techniques and apparatus which produced satisfactory results in the laboratory would not produce the same results with the semi-grounded fluids found in the pipes and tanks of industrial process control. Attempts have been made to solve these problems and obtain in industrial environments that same degree of accuracy obtained in laboratory PH measurements. Basically these solutions involved techniques whereby the PH system was isolated from the pipe or tank environment. See U.S. Pat. Nos. 3,709,796 and 3,732,159 for examples of such systems. However, notwithstanding these prior advances in the art, PH measurements continue to be affected by such problems as voltage gradients within the fluid stream being measured, electronic coupling, external noise picked up by the PH transmission cable, and the insufficient isolation resistance of cable wires.

SUMMARY OF THE INVENTION

Accordingly, it is an object of the present invention to provide a circuit for measuring the PH of fluids in both laboratory and industrial environments.

It is a further object of this invention to provide a PH measuring circuit which combines electronics for isolating the PH environment with a coaxial, symmetrical PH probe.

It is a further object of this invention to provide a PH measuring system which is unaffected by voltage gradients, electronic coupling and external noise pick up.

It is a further object of the present invention to provide a PH measuring circuit wherein the probe and the electronic circuitry required to process the PH signals may be separated by relatively long distances.

The present invention is summarized in that a PH measuring circuit includes a coaxial symmetrical probe having a PH probe surrounded by a reference probe, a shield and a printed circuit foil to which are applied the PH voltage and differential amplifiers for processing the PH and reference signals.

BRIEF DESCRIPTION OF THE DRAWING

The drawing is a schematic circuit diagram of the preferred embodiment of the invention.

DESCRIPTION OF THE PREFERRED EMBODIMENT

The present invention is embodied in a monitoring or measuring circuit illustrated schematically in the drawing. A fluid 10 to be monitored or measured passes through entrance port 12 into a chamber 14, past the sensing and detecting element and thence out exit port 16 and downstream.

Extending into chamber 14 and into the path of the fluid 10 is the coaxial probe, indicated generally at 15. The probe comprises a PH sensitive glass chamber 18 which contains a conductive fluid 20 and a wire conductor 22. A gasket 24 maintains the conductive fluid 20 within glass chamber 18.

An isolating tube 26 surrounds the glass chamber 18 and, together with a porous gasket 28 and another gasket 30, forms a chamber or duct 31 containing a conductive fluid 32 which surrounds a part of the glass chamber 18. A wire conductor 34 extends through gasket 30 into conductive fluid 32. The porous gasket 28, gasket 30, conductive fluid 32 and wire conductor 34 comprise a reference probe which symmetrically surrounds a part of the PH probe comprising the PH sensitive glass chamber 18, the conductive fluid 20, the wire conductor 22 and the gasket 24. Thus, the probe 15 is of coaxial design and has the PH sensing element as its center element. The PH and reference probes are supported by a probe housing 27.

Wire conductor 22 is housed within a cable shielding 36 which extends into the probe housing 27. Conductor 22 passes via a cable 38 to the T2 cable terminal at 44. Reference wire conductor 34 passes via cable 38 to the T3 cable terminal at 48. The cable shield 36 is connected through the T1 cable terminals 40 and 42 to a printed circuit foil or conducting surface 52 at contact point 43.

An operational amplifier IC1 has a noninverting input terminal 54, an inverting input terminal 56 and an output terminal 58. A suitable DC power source supplies IC1 and also IC2 and IC3 but is not shown or described since it forms no part of this invention. Noninverting input 54 is connected through the T2 cable terminals 44 and 46 to the PH probe wire conductor 22. Inverting input 56 is connected through resistor R1, printed circuit contact points 57 and 59 to the output terminal 58. The output terminal 58 likewise is connected through printed circuit contact points 59 and 43, and the T1 cable terminals 40 and 42 to the cable shielding 36. Resistor R1 is chosen to equal the resistance of the PH sensitive glass chamber 18. This design choice will minimize undesirable imbalance of IC current effects from IC1, thereby providing the system with a temperature insensitive feature.

An operational amplifier IC2 has a noninverting input terminal 60, an inverting input terminal 62 and an output terminal 64. Noninverting input 60 is connected through the T3 cable terminals 48 and 50 to the reference wire conductor 34. The inverting input 62 is directly connected through a conductor 63 to the output terminal 64.

The printed circuit foil 52 underlies amplifiers IC1 and IC2, resistor R1 and the conducting elements to and from IC1 and IC2. Since IC1 noninverting input 54 receives the PH signal on conductor 22 through T2 cable terminals 44 and 46, and since IC1 output 58 is directly connected to the printed circuit foil at contact point 59, the printed circuit foil will operate as an active element at the PH voltage. Thus, the PH voltage appearing at cable terminal T2 surrounds the two key amplifiers, IC1 and IC2, so as to isolate the input from larger IC power input or ground voltages. Hence accuracy robbing, humidity loss and board leakage are avoided. Likewise, since the cable shielding 36 is directly connected to the active printed circuit foil at contact point 43, it also will operate as an active element at the PH voltage so as to prevent the relatively weak PH signal from being lost to ground via wire insulation jacket losses.

An operational amplifier IC3 has a noninverting input terminal 66, an inverting input terminal 68 and an output terminal 70. Noninverting input 66 is connected through a resistor R4 to the IC2 output terminal 64 and through a resistor R5 to ground 72 and circuit output terminal 76. Inverting input 68 is connected through a resistor R2 to the printed circuit foil 52 at contact point 61 and, hence, to IC1 output terminal 58. Inverting input 68 also is connected through a resistor R3 to IC3 output terminal 70 and circuit output terminal 74. Since IC3 operates as a differential amplifier the resistances of R2 and R4 are equal to each other, as are the resistances of R3 and R5. IC1, IC2 and IC3 are designed to operate as very high input impedances differential amplifiers.

Any suitable measuring or control device can be connected to the circuit output terminals 74, 76. An indicator M is shown at 78 to be connected across terminals 74 and 76 and may be used to read the PH of fluid 10.

In operation passage of the fluid 10 past the coaxial probe causes the PH sensitive glass chamber 18 to produce a PH voltage between its surfaces. The inside surface voltage on chamber 18 is reflected onto wire conductor 22 through conducting fluid 20, while the outside surface voltage is reflected onto wire conductor 34 through conducting fluid 32. The PH sensitive glass chamber 18 and the conductive fluids 20 and 32 are chosen to best accommodate the particular application as is well known to those skilled in the art.

The glass chamber 18 prevents nearly any current flow between the wire conductors 22 and 34. The PH voltage on wire conductor 22 is passed within shielding 36 and via cable 38 to IC1 noninverting input 54. The cable 38 may be of any convenient length and is not limited to short lengths. In fact the system has performed satisfactorily using cable lengths up to several hundred feet. The reference voltage on wire conductor 34 is passed via cable 38 to IC2 noninverting input 60.

The presence of voltage gradients between the input and exit ports 12 and 16 is a typical occurrence in process stream fluids. Since the PH signal is itself relatively small, even a low magnitude, unwanted additional voltage will cause significant adding to the PH signal and an incorrect PH indication. The present invention inherently avoids the effects of undesirable voltage gradients through the use of a symmetrical, coaxial PH probe which provides a balancing differential action to cancel out any voltage gradient effects. Assuming the existence of a voltage gradient between ports 12 and 16, the voltage gradient effect will be shorted out or balanced through the conductive fluid 32 in duct 31 which surrounds the PH glass chamber 18. The PH is measured by detecting a voltage change (increase or decrease) between the surfaces of glass chamber 18. The outside surface of glass chamber 18 between gaskets 28 and 30 is in contact with conductive fluid 32 and will, therefore, have a voltage equal to that of the fluid 32. Since fluid 32 surrounds glass chamber 18 all parts of chamber 18 within gaskets 28 and 30 willl be at the same reference potential regardless of the existence of a voltage gradient. This feature of the invention solves the problem with prior PH measuring systems wherein the PH and reference probes were separated in the fluid stream so that one of the probes was close to the voltage source, making the system highly susceptible to voltage gradient error. The symmetrical, coaxial probe of the present invention inherently corrects for these voltage gradient problems and provides for accurate measurements even when they exist.

The circuit electronics including IC1, IC2 and IC3 function to preserve and process the PH signal and to allow the conductive fluid 32 to function as the ground reference. It is desirable to mount IC1 at a distance from the probe 15 for such reasons as ease of installation and avoidance of temperature drift of the electronics which could be caused by the temperature of the fluid 10. Thus, ideally the IC1 preamp is located at the system control panel rather than at a remote preamp panel near the probe 15, and such positioning is allowed by automatically adjusting the voltage of cable shielding 36 to the PH voltage appearing at the IC1 output terminal 58. The active cable shielding 36 surrounds the PH signal wire conductor 22 and extends into the probe housing 27. This active shielding feature eliminates the heretofore absolute need to have an amplifier positioned closely to the probe and fluid.

It can thus be seen that the present invention provides a novel PH measuring system including the coaxial probe connected to a balanced differential amplifier, an active printed circuit foil surrounding the PH signal processing elements and an active cable shield that surrounds the PH signal conductor.

Inasmuch as the present invention is subject to many variations, modifications and changes in detail, it is intended that all matter contained in the foregoing description or shown in the accompanying drawing shall be interpreted as illustrative and not in a limiting sense.

What is claimed is:

1. A circuit for measuring the pH of a fluid comprising:
   a pH sensing probe consisting of a pH sensitive glass chamber, a conductive fluid contained in said glass chamber, and a pH conductor extending from a point in contact with said conductive fluid inside said glass chamber to the outside thereof, whereby contact between said fluid and said pH sensitive glass chamber produces a pH signal on said pH conductor;
   a reference probe surrounding said pH sensing probe and coaxial and symmetrical thereto, said reference probe consisting of a cylindrical tube aligned coaxial with said pH sensing probe; first and second gaskets spaced apart and extending between said tube and said glass chamber, whereby a duct surrounding a part of said glass chamber is formed by said gaskets, said tube and said glass chamber; a second conductive fluid contained in said duct; and a reference conductor extending from a point in contact with said second conductive fluid inside said duct to the outside thereof, whereby contact between said fluid and said pH sensitive glass chamber produces a reference signal on said reference conductor;
   a differential amplifier having first and second input terminals and an output terminal, said first input terminal being connected to said pH conductor to receive said pH signal, said second input terminal being connected to said reference conductor to receive said reference signal, whereby said amplifier produces at said output terminal a voltage indicative of said fluid pH;
   a cable shield surrounding said pH conductor and extending between said pH sensing probe and said amplifier, said cable shield being electrically connected to said amplifier output terminal whereby said cable shield has applied thereto a voltage equal in magnitude to the output voltage of said amplifier; and
   indicating means connected to receive said amplifier output for indicating the magnitude of said pH signal.

2. The invention as recited in claim 1, and further comprising a conductive surface underlying said amplifier, said conductive surface being electrically connected to said amplifier output terminal whereby said conductive surface has applied thereto a voltage equal in magnitude to the output voltage of said amplifier.

3. The invention recited in claim 2, and further comprising a cable connected between said pH sensing probe and said amplifier for housing said pH conductor, said cable shield and said reference conductor.

4. The invention as recited in claim 2, wherein said differential amplifier comprises first and second amplifiers, said first amplifier having an input terminal connected to said pH conductor, and an output terminal connected to said cable shield, said conductive surface and to said indicating means, said second amplifier having an input terminal connected to said reference conductor and an output terminal connected to said indicating means.

5. The invention as recited in claim 4, and further comprising a third amplifier having first and second input terminals and an output terminal, said first input terminal being connected to said first amplifier output terminal, said second input terminal being connected to said second amplifier output terminal and said output terminal being connected to said indicating means.

* * * * *